(12) United States Patent
Schmenger et al.

(10) Patent No.: US 7,591,862 B2
(45) Date of Patent: Sep. 22, 2009

(54) DYES FOR KERATINIC FIBERS COMPRISING A SPECIAL ANIONIC THICKENER

(75) Inventors: Jürgen Schmenger, Weiterstadt (DE); Jolanthe Kujawa, Darmstadt (DE); Melanie Bonn, Darmstadt (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/034,124

(22) Filed: Feb. 20, 2008

(65) Prior Publication Data

US 2008/0196174 A1    Aug. 21, 2008

(30) Foreign Application Priority Data

Feb. 20, 2007   (EP)   ................... 07102728
Dec. 10, 2007   (EP)   ................... 07122750

(51) Int. Cl.
*A61Q 5/10* (2006.01)
(52) U.S. Cl. ........................ 8/405; 8/406; 8/435; 8/552; 8/558
(58) Field of Classification Search ............. 8/405, 8/406, 435, 552, 558
See application file for complete search history.

(56) References Cited

U.S. PATENT DOCUMENTS

| | | | |
|---|---|---|---|
| 6,540,791 B1 * | 4/2003 | Dias ................. | 8/111 |
| 2004/0028637 A1 | 2/2004 | Villard | |
| 2004/0143912 A1 | 7/2004 | Legrand et al. | |
| 2004/0202684 A1 * | 10/2004 | Djerassi ................. | 424/401 |
| 2005/0220828 A1 | 10/2005 | Ullom et al. | |
| 2006/0084586 A1 | 4/2006 | Drzewinski et al. | |
| 2006/0162097 A1 | 7/2006 | Schmenger | |

FOREIGN PATENT DOCUMENTS

| | | |
|---|---|---|
| EP | 1428500 | 6/2004 |
| EP | 1496081 | 1/2005 |
| WO | WO 9936445 | 7/1999 |
| WO | WO 01/97772 A1 | 12/2001 |
| WO | WO 2005/044208 A1 | 5/2005 |
| WO | WO 2005044218 | 5/2005 |

OTHER PUBLICATIONS

E. Sagarin, Cosmetics-Science and Technology, 1957, Interscience Publishers Inc., pp. 503-507.
H. Janistyn, "Handbuch der Kosmetika und Riechstoffe" [Handbook of Cosmetics and Fragrance Materials], vol. 3 (1973), pp. 388-397.
K. Schrader in "Grundlagen und Rezepturen der Kosmetika" [Fundamentals and Formulations of Cosmetics], 2nd Edition (1989), pp. 782-815.
PCT Search Report, PCT/IB2008/050611, completed on May 15, 2008, 4 pages.
Arch Personal Care Products: ViscUp EZ press release, "Arch Personal Care Products Builds Viscosity with Exciting New Rheology Modifier", http://www.archchemicals.com/Fed/PC/News/Articles/Aug10_2006.htm.

* cited by examiner

*Primary Examiner*—Eisa B Elhilo
(74) *Attorney, Agent, or Firm*—Melissa G. Krasovec; Idris N. McKelvey

(57) ABSTRACT

The invention relates to compositions for the oxidative or non-oxidative dyeing of keratin fibers, compositions for the simultaneously lightening and coloring of keratin fibers or compositions for the bleaching of keratin fibers, comprising an anionic acrylic thickener obtained by polymerization of (i) 5 to 95 molar percent of at least one monomer performing a weak acid function, and of (ii) 5 to 95 molar percent of at least one monomer performing a strong acid function, wherein such composition exhibits a fraction of water-soluble polymers ranging from 5 to 50 percent by weight of the total polymer, as well as the use of the above anionic acrylic thickener to thicken compositions for the oxidative or non-oxidative dyeing of keratin fibers, compositions for the simultaneously lightening and coloring of keratin fibers or compositions for the bleaching of keratin fibers.

11 Claims, No Drawings

DYES FOR KERATINIC FIBERS COMPRISING A SPECIAL ANIONIC THICKENER

FIELD OF THE INVENTION

The subject matter of the present application are compositions and methods for dyeing keratin fibers comprising a special anionic acrylic polymer as thickener.

BACKGROUND OF THE INVENTION

The object of the invention are thickened compositions for dyeing and/or lightening/bleaching keratin fibers, particularly human hair, that contain direct and/or oxidation dyes and/or bleaching/oxidizing agents and a special thickener, as well as a method for coloring and/or bleaching hair by use of such compositions, Coloring and bleaching compositions are usually in the form of aqueous preferably thickened-solutions or emulsions. Oxidation dyes and bleaching compositions as a rule consist of two components (i) a carrier composition containing the dyes or the bleaching agent and (ii) an oxidizing agent, said components being mixed with one another prior to use and then applied to the hair. Mixing will produce a higher or lower viscosity, depending on the viscosity and mixing ratio of the two components. Normally a good adhesion (i.e. a higher viscosity) of the ready-to-use composition is appreciated. In addition, the hairdressers often needs for their work higher viscosities, for example for special strand or sheet techniques and when special work is to be done with the dye brush or the highlighting brush.

SUMMARY OF THE INVENTION

Hence, a great need existed for economical thickening of the compositions that would ensure good miscibility of said carrier composition with the oxidant and would afford colorants/bleaching compositions with good adhesion properties and coloring/bleaching characteristics.

DETAILED DESCRIPTION OF THE INVENTION

It has now been found that the aforesaid problem can be solved by the use of special anionic acrylic polymers as described in WO 01/97772.

The present invention therefore relates to
a) an agent for the oxidative coloring of keratin fibers, in particular human hair, comprising at least one oxidative dye precursor and at least one anionic acrylic thickener obtained by polymerization of (i) 5 to 95 molar percent of at least one monomer performing a weak acid function, and of (ii) 5 to 95 molar percent of at least one monomer performing a strong acid function, wherein such composition exhibits a fraction of water-soluble polymers ranging from 5 to 50 percent by weight (of the total polymer), preferably from 6 to 35 percent, preferably from 8 to 30 percent;
b) an agent for the non-oxidative coloring of keratin fibers, in particular human hair, comprising at least one direct dye and at least one anionic acrylic thickener obtained by polymerization of (i) 5 to 95 molar percent of at least one monomer performing a weak acid function, and of (ii) 5 to 95 molar percent of at least one monomer performing a strong acid function, wherein such composition exhibits a fraction of water-soluble polymers ranging from 5 to 50 percent by weight (of the total polymer), preferably from 6 to 35 percent, preferably from 8 to 30 percent;
c) an agent for the simultaneously lightening and coloring of keratin fibers, in particular human hair, comprising at least one bleaching agent (e.g. persulfates), at least one dye which is stable in the presence of the used oxidizing agent, and at least one anionic acrylic thickener obtained by polymerization of (i) 5 to 95 molar percent of at least one monomer performing a weak acid function, and of (ii) 5 to 95 molar percent of at least one monomer performing a strong acid function, wherein such composition exhibits a fraction of water-soluble polymers ranging from 5 to 50 percent by weight (of the total polymer), preferably from 6 to 35 percent, preferably from 8 to 30 percent;
d) an agent for the bleaching of keratin fibers, in particular human hair, comprising at least one bleaching agent (e.g. persulfates) and at least one anionic acrylic thickener obtained by polymerization of (i) 5 to 95 molar percent of at least one monomer performing a weak acid function, and of (ii) 5 to 95 molar percent of at least one monomer performing a strong acid function, wherein such composition exhibits a fraction of water-soluble polymers ranging from 5 to 50 percent by weight (of the total polymer), preferably from 6 to 35 percent, preferably from 8 to 30 percent;
e) an agent for the simultaneously lightening and coloring of keratin fibers, in particular human hair, which is mixed with an oxidizing agent (e.g. hydrogen peroxide) prior to use, comprising at least one dye which is stable in the presence of the used oxidizing agent, and at least one anionic acrylic thickener obtained by polymerization of (i) 5 to 95 molar percent of at least one monomer performing a weak acid function, and of (ii) 5 to 95 molar percent of at least one monomer performing a strong acid function, wherein such composition exhibits a fraction of water-soluble polymers ranging from 5 to 50 percent by weight (of the total polymer), preferably from 6 to 35 percent, preferably from 8 to 30 percent.

Especially preferred are anionic acrylic polymers wherein said monomer performing a weak acid function is selected from the group consisting of acrylic acid, methacrylic acid, itaconic acid, crotonic acid, maleic acid and fumaric acid and said monomer performing a strong acid function is selected from the group consisting of monomers having a function of the sulfonic acid type or phosphonic acid type, such as 2-acrylamido-2-methylpropane sulfonic acid (AMPS).

Furthermore the anionic acrylic polymer may be crosslinked (or branched) by one of the following crosslinking agents: methylene bisacrylamide (MBA), ethylene glycol diacrylate, polyethylene glycol dimethacrylate, diacrylamide, cyanomethacrylate, vinyloxyethacrylate or methacrylate, formaldehyde, glyoxal, and compositions of the glycidylether type such as ethyleneglycol diglycidylether, or epoxydes.

Particularly preferred anionic acrylic thickeners are Sodium Acrylate/Sodium Acryloyldimethyl Taurate Copolymers. A particularly suitable anionic acrylic thickeners with the INCI name Sodium Acrylate/Sodium Acryloyldimethyl Taurate Copolymer & Hydrogenated Polydecene & Sorbitan Laurate & Trideceth-6 is marketed by Arch Personal Care Products, South Plainfield, USA under the tradename ViscUp® EZ. For further details of the structure and the preparation of said anionic acrylic thickeners reference is made to WO 01/97772; that herewith is explicitly incorporated herein by reference.

The anionic acrylic thickener is preferably contained in the agent of the invention in an amount from 0.01 to 8.0 percent by weight and particularly from 0.1 to 5 percent by weight (based on the active substance).

If the agent according to the invention is the agent for the oxidative coloring of keratin fibers (a) it comprises oxidative hair dye precursors that will deliver a variety of hair colors to the hair. These small molecules are activated by an oxidizing agent or air oxygen and react with further molecules to form a larger colored complex in the hair shaft. Suitable oxidative hair dye precursors are developers, couplers and compounds coupling with themselves The developers may be used alone or in combination with other developers (also known as primary intermediates), and one or more may be used in combination with one or more couplers. Couplers (also known as color modifiers or secondary intermediates) are generally colorless molecules that can form colors in the presence of activated developers, and are used with other developers or couplers to generate specific color effects or to stabilize the color. The choice of developers and couplers will be determined by the color, shade and intensity of coloration that is desired. The developers and couplers may be used herein, singly or in combination, to provide dyes having a variety of shades ranging from ash blonde to black.

Suitable oxidative hair dye precursors are, for example, the following developers, couplers and compounds coupling with themselves:

Developers: p-phenylenediamine derivatives; p-aminophenol derivatives and heterocyclic derivatives, such as: 1,4-diamino-2,6-dimethylbenzene, 1,4-diamino-2,5-dimethylbenzene, 1,4-diamino-2,3-dimethylbenzene, 2-chloro-1,4-diaminobenzene, 4-phenylaminoaniline, 1,4-diamino-2-methoxymethylbenzene, 4-dimethylaminoaniline, 4-diethylamino-aniline, 4-[di(2-hydroxyethyl)amino]aniline, 4-[(2-methoxyethyl)amino]-aniline, 4-[(3-hydroxypropyl) amino]aniline, 1,4-diamino-2-(2-hydroxyethyl)benzene, 1,4-diamino-2-(1-methylethyl) benzene, 1,3-bis-[(4-aminophenyl)-(2-hydroxyethyl)amino]-2-propanol, 1,8-bis-(2,5-diaminophenoxy)-3,6-dioxaoctane, 4-aminophenol, 4-amino-3-methylphenol, 4-methyl-aminophenol, 4-amino-2-(aminomethyl)phenol, 4-amino-2-[(2-hydroxyethyl) amino]-]-methylphenol, 4-amino-2-(methoxymethyl)phenol, 4-amino-2-(2-hydroxyethyl)phenol, 5-amino-salicylic acid, 2,5-diaminopyridine, 2,4,5,6-tetramino-pyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)-methyl]-1H-pyrazole, 1-[(4-chlorophenyl)methyl]-4,5-diamino-1H-pyrazole, 4,5-diamino-1-methyl-1H-pyrazole, 4,5-diamino-3-methyl-1-phenyl-1H-pyrazole, 4,5-diamino-1-(2-hydroxyethyl)-3-methyl-1H-pyrazole, 2-amino-phenol, 2-amino-6-methylphenol and 2-amino-5-methyl-phenol, or their salts.

Couplers: phenols, resorcinols and naphthol derivatives, such as: N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di-[(2-hydroxyethyl)amino]-1,5-dimethoxybenzene, 2,3-diamino-6-methoxypyridine, 3-amino-6-methoxy-2-(methylamino)-pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1-(3-hydroxypropoxy)benzene, 1-(2-aminoethoxy)-2,4-diaminobenzene, 2-amiono-1-(2-hydroxyethoxy)-4-methylaminobenzene, 2,4-diaminophenoxyacetic acid, 3-[di(2-hydroxyethyl)-amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di-(2,4-diaminophenoxy)methane, 1,3-di-amino-2,4-dimethoxybenzene, 2,6-bis-(2-hydroxyethyl) aminotoluene, 4-hydroxyindol, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methyl-phenol, 3-amino-phenol, 2-[(3-hydroxyphenyl)amino]acetamide, 5-[(2-hydroxyethyl)amino]-2-methylphenol, 3-[(2-hydroxyethyl)amino]-phenol, 3-[(2-methoxy-ethyl)amino]-phenol, 5-amino-2-ethylphenol, 2-(4-amino-2-hydroxyphenoxy)-ethanol, 5-[(3-hydroxypropyl)amino]-2-methylphenol, 3-[(2,3-dihydroxypropyl)-amino]-2-methyl-phenol, 3-[(2-hydroxyethyl)amino]-2-methylphenol, 2-amino-3-hydroxy-pyridine, 5-amino-4-chloro-2-methylphenol, 1-naphthol, 1,5-dihydroxy-naphthalene, 1,7-dihydroxy-naphthalene, 2,3-dihydroxynaphthalene, 2,7-dihydroxynaphthalene, 2-methyl-1-naphthol acetate, 1,3-dihydroxy-benzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene,3,4-methylenedioxyphenol, 3,4-methylenedioxyaniline, 5-[(2-hydroxyethyl)amino]-1,3-benzodioxole, 6-bromo-1-hydroxy-3,4-methylendioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxy-indole, 6-hydroxyindole, 7-hydroxy-indole and 2,3-indolindione, or their salts; and 2-amino-5-methylphenol; 2-amino-6-methylphenol, 2-amino-5-ethoxyphenol or 2-propylamino-5-aminopyridine.

The hair dye compositions of the present invention will generally comprise from 0.001% to 15% by weight of dye precursors. For example compositions providing low intensity dyeing such as natural blond to light brown hair shades generally comprise from 0.001% to 7% by weight, preferably from 0.1% to 5% by weight, more preferably from about 0.2% to 2% by weight of dyeing composition of precursors and couplers. Darker shades such as browns and black typically comprise from 0.001% to 15% by weight, preferably from 0.05% to 10% by weight, more preferably form 1% to 5% by weight of precursors and couplers.

The developer substances and coupler substances are generally used in approximately equimolar amounts; however, it is not disadvantageous if the developer substances are present in this regard in a certain excess or deficit, for example a coupler:developer ratio of 1:3 to 1:0.3.

To achieve certain color shades, the agent for the oxidative coloring of keratin fibers (a) may also contain common natural and/or synthetic direct dyes, for example vegetable dyes such as henna or indigo, triphenylmethane dyes, aromatic nitro dyes, azo dyes, quinone dyes or cationic or anionic dyes.

The agent for the oxidative coloring of keratin fibers (a) will generally comprise from 0.001 percent to 10 percent by weight of direct dyes, preferably from 0.1 percent to 5 percent by weight, more preferably from 0.2 percent to 2 percent by weight.

Other common dyes known to be used for coloring hair and which can be contained in the colorant of the invention are described by, among others, E. Sagarin in pages 503 ff, by H. Janistyn in, "Handbuch der Kosmetika und Riechstoffe" [Handbook of Cosmetics and Fragrance Materials"], vol. 3 (1973), pages 388 ff, and by K. Schrader in "Grundlagen und Rezepturen der Kosmetika" [Fundamentals and Formulations of Cosmetics], 2nd Edition (1989), pages 782-815.

If the agent according to the invention is the agent for the non-oxidative coloring of keratin fibers (b) (which is free of oxidative dye precursors and oxidizing agents) it contains at least one of the aforesaid direct dyes in the aforesaid amounts.

If the agent according to the invention is the agent for the simultaneously lightening and coloring of keratin fibers (c) it comprises at least one oxidizing agent (e.g. hydrogen peroxide or persulfates) and at least one dye that is stable in the presence of the used oxidizing agent.

As oxidation-stable dyes may be especially used the following dyes: 3-(2',6'-diaminopyridyl-3'-azo) pyridine (=2,6-diamino-3-[(pyridin-3-yl)azo]pyridine), 2-((4-eth-yl(2-hydroxyethyl)amino)-2-methylphenyl) azo-5-nitro-1,3-thiazole (Disperse Blue 106), N,N-di(2-hydroxyethyl)-3-methyl-4-[(4-nitrophenyl)azo]aniline (Disperse Red 17; C.I. 11210), 3-diethylamino-7-(4-dimethylaminophenylazo)-5-phenylphenazinium chloride (C.I. 11050), 4-(2-thiazolylazo) resorcinol, 4-[(4-phenylamino)azo]benzenesulfonic acid sodium salt (Orange IV), 1-[(3-aminopropyl)amino]-9,10-anthracenedione (HC Red No. 8), 3',3",4,5,5',5",6,7-octabromo-phenolsulfonphthalein (Tetrabromophenol Blue), 1-[(4-amino-3,5-dimethylphenyl)-(2,6-dichlorophenyl) methylene]-3,5-dimethyl-4-imino-2,5-cyclohe-xadiene-phosphoric acid (1:1) (Basic Blue 77), 3',31",51",5"-tetrabromo-m-cresolsulfon-phthalein, 2,4-dinitro-1-naphthol-7-sulfonic acid disodium salt (Acid Yellow 1; C.I. 10316), 4-[2'-hydroxy-1'-naphthyl)azo]benzene]sulfonic acid sodium salt (Acid Orange 7; C.I. 15510), 3',6'-dihydroxy-2',4',5',7'-tetraiodospiro[isobenzofuran-1(3H), 9'(9H)xanthen-]-3-one disodium salt (Acid Red 51; C.I. 45430), 6-hydroxy-5-[(2-methoxy-5-methyl-4-sulfophe-nyl)azo]-2-naphthalene-sulfonic acid disodium salt (FD&C Red 40; C.I. 16035), 2,4-dini-tro-1-naphthol sodium salt (Acid Yellow 24; C.I. 10315), 2',4',5',7'-tetrabromo-4,5,6,7-tetrachloro-3', 6'-dihydroxyspiro {isobenzofuran-1(3H), 9'[9H]xanthen}-3-one disodium salt (Acid Red 92; C.I. 45410),4-(2-hydroxy-1-naphthylazo)-3-methylbenzenesulfonic acid so-dium salt (Acid Orange 8; C.I. 15575), 2-amino-1,4-naphthalenedione, dithizone (1,5-diphenyl-thiocarbazone). Nevertheless it is also possible to use one or more of the aforementioned direct dyes if they are stable against the bleaching/oxidizing agent used.

Preferred bleaching agents are inorganic perhydrate salt bleaching compounds, such as the alkali metal salts of perborates, percarbonates, perphosphates, persilicates, persulphates and the like. Especially preferred are persulphate salts, such as ammonium persulate, sodium persulfate or potassium persulfate. The bleaching agents are usually present in the agent (d) or (e) in an amount of from 5 to 65 percent by weight, preferably 20 to 50 percent by weight. The bleaching agents may especially be provided in the form of a non-aqueous cream or as a powder which is dissolved prior to use.

The agents (a), (c), (d) and (e) are used in combination with one or more known oxidants, whereas the bleaching agent (d) preferably comprises a combination of persulfates and hydrogen peroxide. Any oxidizing agent known in the art (including air-oxygen and enzyme-based oxidizing systems) may be utilized in the present invention. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide.

These inorganic perhydrate salts may be incorporated as monohydrates, tetrahydrates etc. Alkyl and aryl peroxides, and or peroxidases may also be used. Mixtures of two or more such oxidizing agents may also be used if desired.

The oxidizing agents may be provided in aqueous solution or as a powder which is dissolved prior to use. Especially preferred for use in the compositions according to the present invention is hydrogen peroxide, alone or in combination with other oxidants.

According to the present invention the compositions comprise from 0.1% to 15% by weight, preferably from 1% to 10% by weight, and most preferably from 2% to 7% by weight of an oxidizing agent.

Another preferred oxidizing agent for use herein is a source of peroxymonocarbonate ions. Preferably such a source is formed in situ from a source of hydrogen peroxide and a hydrogen carbonate ion source. Such an oxidizing agent has been found to be particularly effective at a pH of up to and including 9.5, preferably 7.5 to 9.5 more preferably pH 9. Moreover, this system is also particularly effective in combination with a source of ammonia or ammonium ions. It has been found that this oxidizing agent can deliver improvements to the desired hair colour results particularly with regard to the delivery of high lift, whilst considerably reducing the odour, skin and scalp irritation and damage to the hair fibres.

According to the present invention the compositions comprise from 0.1% to 15% by weight, preferably from 1% to 10% by weight, and most preferably from 1% to 8% by weight of a hydrogencarbonate ion and from 0.1% to 10% by weight, preferably from 1% to 7% by weight, and most preferably from 2% to 5% by weight of a source of hydrogen peroxide.

According to the present invention the composition may further optionally comprise at least one source of alkalizing agent, preferably a source of ammonium ions and or ammonia. Any agent known in the art may be used such as alkanolamides for example monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol and guanidium salts. Particularly, preferred alkalizing agents are those which provide a source of ammonium ions. Any source of ammonium ions is suitable for use herein. Preferred sources include ammonium chloride, ammonium sulphate, ammonium nitrate, ammonium phosphate, ammonium acetate, ammonium carbonate, ammonium hydrogen carbonate, ammonium carbamate, ammonium hydroxide, ammonia and mixtures thereof. Particularly preferred are ammonium carbonate, ammonium carbamate, ammonium hydrogen carbonate, ammonia and mixtures thereof. The compositions of the present invention may comprise from 0.1% to 10% by weight, preferably from 0.5% to 5% by weight, most preferably from 1% to 3% by weight, of an alkalizing agent, preferably ammonium ions.

According to the present invention the compositions may further comprise a source of radical scavenger. As used herein the term radical scavenger refers to a species that can react with a reactive radical, preferably carbonate radicals, to convert the reactive radical by a series of fast reactions to a less reactive species.

Preferred radical scavengers according to the present invention are selected from the classes of alkanolamines, amino sugars, amino acids, esters of amino acids and mixtures thereof. Particularly preferred compounds are: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, and mixtures thereof, and the salts such as the potassium, sodium and ammonium salts thereof and mixtures thereof. Especially preferred compounds are glycine, sarcosine, lysine, serine, 2 methoxyethylamine, glucosamine, glutamic acid, morpholine, piperidine, ethylamine, 3 amino-1-propanol and mixtures thereof.

The radical scavengers according to the present invention preferably have a molecular weight of less than 500, preferably less than 300, more preferably less than 250 in order to facilitate penetration of the radical scavenger into the hair fibre. The compositions of the present invention preferably comprise from 0.1% to 10% by weight, preferably from 1% to 7% by weight of radical scavenger. The radical scavenger is also preferably selected such that it is not an identical species as the alkalizing agent. According to one embodiment of the present invention the radical scavenger may be formed in situ in the hair dyeing compositions prior to application to the hair fibres.

The compositions of the present invention may further comprise additional ingredients which include, but are not limited to, additional thickeners other than the above mentioned special anionic acrylic thickener, solvents, enzymes, surfactants, conditioning agents, carriers, antioxidants or reducing agents, stabilizers, chelants, perfumes, hair swelling agents and/or polymers. Some of these additional components are detailed hereafter.

The pH of the agent for the non-oxidative coloring of keratin fibers based on direct dyes, the pH of the colorant of the invention is in the range from 5 to 10 and preferably from 6 to 9, whereas the pH of the agent for the oxidative coloring of keratin fibers based on oxidation dye precursors is from 6 to 12 and preferably from 9 to 11. The pH of the ready-to-use oxidation hair colorant (namely of the mixture of the hair colorant of the invention and the oxidant) and the reday-to-use agent for the simultaneously lightening and coloring of keratin fibers is from 5,5 to 10 and preferably from 6 to 9. The pH of the ready-to-use agent for the bleaching of keratin fibers is from 8 to 12 and preferably from 9 to 11.5.

Depending on the composition and the desired pH, the pH is preferably adjusted with ammonia or an organic amine, for example glucamine, aminomethylpropanol, monoethanolamine or triethanolamine, with an inorganic base, for example sodium hydroxide, potassium hydroxide, sodium carbonate or calcium hydroxide, or with an organic or inorganic acid, for example lactic acid, citric acid, acetic acid or phosphoric acid.

The ready-to-use compositions may be, for example, a solution, especially an aqueous or aqueous-alcoholic solution. However a particularly preferred form of the composition according to the invention is a cream, a gel or an emulsion. Its composition comprises a mixture of the dye and/or lightening/bleaching ingredients with the conventional additive ingredients usually used in this type of preparation.

According to a preferred embodiment of the present invention dye powders or dye granules or bleaching powders or bleaching granules are mixed with an appropriate carrier mass prior to use to form the ready-to-use composition. Particularly preferred is the use of pellets as described in WO 2005/044208 which are mixed with an appropriate carrier mass prior to use to form the ready-to-use composition. WO 2005/044208 herewith is explicitly incorporated herein by reference.

To attain simultaneous lightening and coloring of the fibers, the dye-containing pellets of the invention can also contain an ammonium carbonate, for example ammonium hydrogen carbonate, or an amino acid or a salt thereof, for example sodium glycinate.

Depending on the intended use, the composition (a), (b), (c), (d) or (e) according to the invention can be used with one or more oxidizing agents (lightening/bleaching; oxidation colorants) or without an oxidizing agent (non-oxidative colorants).

When used for the oxidative dyeing of keratin fibers, the afore described composition (a) is mixed with an oxidant just before use, and an amount of the ready-to-use mixture sufficient for dyeing, as a rule 60 to 200 grams, is applied to the fibers.

If the colorant of the invention contains no oxidation dye precursors or if it contains oxidation dye precursors that are readily oxidized by atmospheric oxygen, said colorant can be applied to the keratin fibers directly without previous mixing with an oxidant.

Suitable oxidants for developing the coloration are described above, whereas a hydrogen peroxide, or its addition compounds with urea, melamine or sodium bromate, in the form of a 1 to 12 percent by weight, preferably 6 percent by weight, aqueous solution, is preferred as the oxidizing agent. The mixing ratio of composition (a) to oxidant depends on the concentration of the oxidant and as a rule is 5:1 to 1:2 and preferably 1:1, the amount of oxidant in the ready-to-use composition being preferably 0.5 to 8 weight percent and particularly 1 to 4 weight percent. The ready-to-use colorant is allowed to act on the keratin fibers (for example human hair) at 15° C. to 50° C. for 10 to 45 minutes and preferably for 15 to 30 minutes after which the fibers are rinsed with water and dried. Optionally, following this rinsing, the keratin fibers are washed with a shampoo and possibly post-rinsed with a weak organic acid, for example tartaric acid. The keratin fibers are then dried.

The agent for the simultaneously lightening and coloring of keratin fibers (c) or (e) as well as the agent for the bleaching of keratin fibers (d) is normally used in the form of multi-component-kits, especially two-component-kits, wherein one component contains the oxidant and the other contains the dyes or the bleaching agents. Prior to use the components are mixed with each other and an amount of the ready-to-use mixture sufficient for coloring and/or lightening/bleaching the keratin fibers, as a rule 60 to 200 grams, is applied to the fibers. The ready-to-use composition is allowed to act on the keratin fibers (for example human hair) at 15° C. to 50° C. for 10 to 45 minutes and preferably for 15 to 30 minutes after which the fibers are rinsed with water and dried. Optionally, following this rinsing, the keratin fibers are washed with a shampoo and possibly post-rinsed with a weak organic acid, for example tartaric acid. The keratin fibers are then dried.

If necessary, the viscosity of the ready-to-use compositions (a), (b), (c) or (d) can be increased by adding an appropriate amount of the above described anionic acrylic thickener of the invention to the composition. It is also possible to thicken oxidative or non-oxidative colorants or agents for simultaneously lightening and dyeing keratin fibers or agents for bleaching keratin fibers by addition of the above described anionic acrylic thickener of the invention just prior to use. This provides simpler and more economical basic formulations.

The above described compositions (a), (b), (c) or (d) meet the requirements in terms of adhesion properties, application characteristics and viscosity adjustment in outstanding manner and are clearly easier to apply. Moreover, the above described composition s (a), (b), (c) or (d) have a uniform consistency and are cosmetically appealing. Particularly notable is the very good viscosity and outstanding stability of the above described composition s (a), (b), (c) or (d) and their excellent adhesion to hair. Furthermore, the use of the above described compositions (a), (c) or (d) makes it possible to vary the weight ratio of colorant to oxidant over a wide range (for example from 1:1 to 1:2.5) without adversely affecting the viscosity and adhesion properties of the ready-to-use oxidation colorant in an appreciable manner.

The following examples are intended to explain the subject matter of the invention more closely without limiting its scope.

EXAMPLES

Example 1

Oxidation Hair Colorant, Liquid

| | |
|---|---|
| 0.5000 g | ViscUp ®EZ of Arch Personal Care Products, South Plainfield, USA [1] |
| 5.0000 g | 2-octyl-1-dodecanol (Eutanol G, supplied by Cognis/Germany) |
| 15.0000 g | oleic acid |
| 10.0000 g | sodium lauryl alcohol diethylene glycol ether sulfate (28% aqueous solution) |
| 1.3620 g | 4-aminophenol |
| 0.5000 g | 1-naphthol |
| 0.0136 g | resorcinol |
| 0.0034 g | 2-amino-6-chloro-4-nitrophenol |
| 12.0000 g | ammonia, 25% aqueous solution |
| 1.0000 g | disodium ethylenediaminetetraacetate |
| 1.0000 g | ascorbic acid |
| 15.0000 g | isopropanol |
| Balance | water |

Just before use, 50 g of the foregoing hair colorant was mixed with 50 g of a 6% aqueous hydrogen peroxide solution. This gave a homogeneous, cosmetically appealing, optimally thickened, colorant formulation. The mixture thus obtained was then applied to naturally blond hair. After an exposure time of 30 min at 40° C., the hair was rinsed with water and dried. The hair showed a bright copper-red coloration.

Example 2

Oxidation Hair Colorant in Gel Form

| | |
|---|---|
| Component (A): Liquid Dye Carrier Composition | |
| 1.20 g | ViscUp ®EZ of Arch Personal Care Products, South Plainfield, USA [1] |
| 10.00 g | of lauryl alcohol |
| 6.00 g | nonylphenol ethoxylated with 4 moles of ethylene oxide |
| 6.00 g | oleic acid |
| 0.62 g | 2-(methoxymethyl)-benzene-1,4-diamine |
| 0.28 g | resorcinol |
| 5.00 g | sodium lauryl alcohol diethylene glycol ether sulfate, 28% aqueous solution |
| 1.00 g | disodium ethylenediaminetetraacetate |
| 18.00 g | ammonia, 25% aqueous solution |
| 8.00 g | ethanol |
| Balance | water |
| Component (B): Hydrogen Peroxide Emulsion | |
| 10.0 g | cetylstearyl alcohol |
| 1.5 g | cholesterol |
| 4.0 g | sodium lauryl alcohol diethylene glycol ether sulfate, 28% aqueous solution |
| 35.0 g | hydrogen peroxide, 35% aqueous solution |
| 0.3 g | perfume |
| Balance | water |

Before use, 40 g of the liquid dye carrier composition (A) was mixed with 80 g of the hydrogen peroxide emulsion (B), corresponding to an (A):(B) mixing ratio of 1:2, and 120 g of this mixture was applied to gray human hair. After an exposure time of 20 min at room temperature, the hair was rinsed with water and dried. The hair treated in this manner was colored uniformly brown from hairline to hair tips. The colorant of the invention was easily applied and did not run off the hair.

Example 3

Oxidation Hair Colorant in Cream Form

| | |
|---|---|
| 0.40 g | sodium acrylate/sodium acryloyldimethyl taurate copolymer |
| 3.00 g | oleyl alcohol |
| 15.00 g | cetyl alcohol |
| 3.50 g | sodium lauryl alcohol diethylene glycol ether sulfate (28% aqueous solution) |
| 3.00 g | monoethanolamine |
| 1.30 g | 1-methyl-2,5-diaminobenzene |
| 1.00 g | beeswax |
| 0.65 g | resorcinol |
| 0.50 g | keratin hydrolyzate |
| 0.50 g | silk protein hydrolyzate |
| 0.50 g | 2-amino-6-chloro-4-nitrophenol |
| 0.30 g | ascorbic acid |
| Balance | water |

Just before use, 50 g of the foregoing hair colorant was mixed with 50 g of 12% aqueous hydrogen peroxide solution. The resulting mixture was then applied to naturally blond hair. After an exposure time of 30 min at 40° C., the hair was rinsed with water and dried. A uniform, strong brown shade was obtained.

Example 4

Hair Tinting Agent (Non-Oxidative)

| | |
|---|---|
| 2.5 g | ViscUp ®EZ of Arch Personal Care Products, South Plainfield, USA [1] |
| 6.0 g | lauryl alcohol |
| 5.0 g | sodium lauryl sulfate |
| 1.5 g | 2-amino-6-chloro-4-nitrophenol |
| 1.0 g | monoethanolamine |
| 1.0 g | beeswax |
| 0.5 g | keratin hydrolyzate |
| 0.3 g | silk protein hydrolyzate |
| 0.2 g | glycine |
| Balance | water |

A slightly gelled colorant composition was obtained which because of its outstanding viscosity characteristics was easily and uniformly applied and adhered well to the hair. After an exposure time of 20 min at 20° C., the hair was rinsed with luke-warm water, styled and dried. The hair treated in this manner showed a uniform, very lustrous gold-orange coloration.

Example 5

Oxidative Colorant

| | Component (A): Dye Carrier Composition |
|---|---|
| 4.0 g | ViscUp ®EZ of Arch Personal Care Products, South Plainfield, USA [1] |
| 8.0 g | 2-octyl-1-dodecanol (Eutanol G, supplied by Cognis/Germany) |
| 3.0 g | sodium lauryl alcohol diethylene glycol ether sulfate (28% aqueous solution) |
| 2.8 g | 2,5-diaminotoluene sulfate |
| 1.0 g | resorcinal |
| 0.4 g | m-aminophenol |
| 0.2 g | 2-amino-4-(2'-hydroxyethylamino)anisole sulfate |
| 0.3 g | ascorbic acid |
| 0.1 g | ethylenediaminetetraacetic acid |
| 12.2 g | ammonia, 25% aqueous solution |
| 2.0 g | ethanol |
| Balance | water |

| | Component (B): Hydrogen Peroxide - Emulsion |
|---|---|
| 10.0 g | cetylstearyl alcohol |
| 1.5 g | cholesterol |
| 4.0 g | sodium lauryl alcohol diethylene glycol ether sulfate, 28% aqueous solution |
| 17.0 g | hydrogen peroxide, 35% aqueous solution |
| 0.3 g | perfume |
| Balance | water |

Before use, 40 g of the liquid dye carrier composition (A) was mixed with 80 g of the hydrogen peroxide emulsion (B), corresponding to an (A):(B) mixing ratio of 1:2, and 120 g of this mixture was applied to human hair. After an exposure time of 20 min at room temperature, the hair was rinsed with water and dried. The hair treated in this manner was of a uniform, dark-brown shade. The colorant of the invention adhered very well to the hair without running off.

Example 6

Colorant for Simultaneously Lightening and Coloring Hair

| | Component (A): Dye Carrier Composition |
|---|---|
| 4.0 g | ViscUp ®EZ of Arch Personal Care Products, South Plainfield, USA [1] |
| 2.0 g | 4-dimethylaminophenylazo-2N-methyl-5N-methyl-imidazolium chloride |
| 8.0 g | 2-octyl-1-dodecanol (Eutanol G, supplied by Cognis/Germany) |
| 3.0 g | sodium lauryl alcohol diethylene glycol ether sulfate (28% aqueous solution) |
| 8.0 g | ammonia, 25% aqueous solution |
| 0.1 g | ethylenediaminetetraacetic acid |
| 2.0 g | ethanol |
| Balance | water |
| | Component (B): Hydrogen Peroxide - Emulsion |
| 10.0 g | cetylstearyl alcohol |
| 1.5 g | cholesterol |
| 4.0 g | sodium lauryl alcohol diethylene glycol ether sulfate, 28% aqueous solution |
| 17.0 g | hydrogen peroxide, 35% aqueous solution |
| 0.3 g | perfume |
| Balance | water |

Before use, 40 g of the liquid dye carrier composition (A) was mixed with 40 g of the hydrogen peroxide emulsion (B), corresponding to an (A):(B) mixing ratio of 1:1, and this mixture was applied to human hair. After an exposure time of 10 min at room temperature, the hair was rinsed with water and dried. The colorant of the invention adhered very well to the hair without running off.

Example 7

Colorant for Simultaneously Lightening and Coloring Hair

| | Lightening Powder (A): |
|---|---|
| 20.0 g | potassium persulfate |
| 30.0 g | ammonium persulfate |
| 24.0 g | sodium silicate |
| 12.5 g | magnesium oxide |
| 6.0 g | soap beads |
| 2.0 g | dispersed silicic acid |
| 0.5 g | ethylenediaminetetraacetic acid disodium salt |
| 0.1 g | Acid Red 92 (CI 45410) |
| 0.2 g | Acid Yellow 1 (CI 10316) |
| 0.8 g | Acid Yellow 24 (CI 10315) |

| | -continued |
|---|---|
| 1.0 g | Acid Orange No 8 (CI 15575) |
| 1.0 g | Acid Orange No 7 (CI 15510) |
| | Thickener (B): |
| 100.00 g | ViscUp ®EZ of Arch Personal Care Products, South Plainfield, USA [1] |

[1] ViscUp ®EZ is a mixture of 35-55% Sodium Acrylate/Sodium Acryloyldimethyl Taurate Copolymer and 23-35% Hydrogenated Polydecene and 20-30% Sorbitan Laurate and 5-10% Trideceth-6

Before use, 40 g of the above lightening powder (A) was mixed with 80 g of a 12% aqueous hydrogen peroxide solution (C) and 5 g of the above thickener (B) to form a homogeneous composition. This mixture was applied to dry human hair. After an exposure time of 20 min at 40° C., the hair was rinsed with warm water and dried. The hair treated in this manner was of a uniform, bright orange shade. The colorant of the invention adhered very well to the hair without running off.

Unless otherwise indicated, all percentages in the present patent application are by weight.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition for the oxidative coloring of keratin fibers, comprising at least one oxidative dye precursor, at least one thickener comprising at least one anionic acrylic copolymer obtained by polymerization of i.) 5 to 95 molar percent of at least one monomer performing a weak acid function, and of ii.) 5 to 95 molar percent of at least one monomer performing a strong acid function, wherein said copolymer exhibits a water-soluble fraction ranging from 5 to 50 percent by weight of the total copolymer, 23-35% hydrogenated polydecene, 20-30% sorbitan laurate, and 5-10% trideceth-6.

2. A composition for the non-oxidative coloring of keratin fibers, comprising at least one direct dye, at least one thickener comprising at least one anionic acrylic copolymer obtained by polymerization of i.) 5 to 95 molar percent of at least one monomer performing a weak acid function, and of ii.) 5 to 95 molar percent of at least one monomer performing a strong acid function, wherein said copolymer exhibits a water-soluble fraction ranging from 5 to 50 percent by weight of the total copolymer, 23-35% hydrogenated polydecene, 20-30% sorbitan laurate, and 5-10% trideceth-6.

3. A composition for the simultaneously lightening and coloring of keratin fibers, comprising at least one bleaching agent, at least one thickener comprising at least one anionic acrylic copolymer obtained by polymerization of i.) 5 to 95 molar percent of at least one monomer performing a weak acid function, and of ii.) 5 to 95 molar percent of at least one monomer performing a strong acid function, wherein said copolymer exhibits a water-soluble fraction ranging from 5 to 50 percent by weight of the total copolymer, 23-35% hydrogenated polydecene, 20-30% sorbitan laurate, and 5-10% trideceth-6.

4. An agent for the bleaching of keratin fibers, comprising at least one bleaching agent, at least one thickener comprising at least one anionic acrylic copolymer obtained by polymerization of i.) 5 to 95 molar percent of at least one monomer performing a weak acid function, and of ii.) 5 to 95 molar percent of at least one monomer performing a strong acid function, wherein said copolymer exhibits a water-soluble fraction ranging from 5 to 50 percent by weight of the total copolymer, 23-35% hydrogenated polydecene, 20-30% sorbitan laurate, and 5-10% trideceth-6.

5. An agent for the simultaneously lightening and coloring of keratin fibers, which is mixed with an oxidizing agent prior to use, comprising at least one dye which is stable in the presence of the used oxidizing agent, at least one thickener comprising at least one anionic acrylic copolymer obtained by polymerization of i.) 5 to 95 molar percent of at least one monomer performing a weak acid function, and of ii.) 5 to 95 molar percent of at least one monomer performing a strong acid function, wherein said copolymer exhibits a water-soluble fraction ranging from 5 to 50 percent by weight of the total copolymer, 23-35% hydrogenated polydecene, 20-30% sorbitan laurate, and 5-10% trideceth-6.

6. An agent according to claim 1, wherein the monomer performing a weak acid function is selected from the group consisting of acrylic acid, methacrylic acid, itaconic acid, crotonic acid, maleic acid and fumaric acid.

7. An agent according to claim 1, wherein the monomer performing a strong acid function is selected from the group consisting of monomers having a function of the sulfonic acid type or phosponic acid type, such as 2-acrylamido-2-methyl-propane sulfonic acid.

8. An agent according to claim 7, wherein the monomer performing a strong acid function is 2-acrylamido-2-methl-propane sulfonic acid.

9. An agent according to claim 1, characterized in that the anionic acrylic copolymer is crosslinkled or branched by a crosslinking agent which is selected from the group consisting of methylene bisacrylamide, ethylene glycol diacrylate, polyethylene glycol dimethacrylate, diacrylamide, cyanomethacrylate, vinyloxyethacrylate, methacrylate, formaldehyde, glyoxal, compositions of the glycidylether type and epoxydes.

10. An agent according to claim 1, wherein the anionic acrylic copolymer comprises a Sodium Acrylate/Sodium Acryloyldimethyl Taurate.

11. An agent according to claim 1, comprising the thickener in an amount from 0.01 to 8.0 percent by weight, based on the active substance.

* * * * *